United States Patent [19]

Gentz et al.

[11] Patent Number: 5,696,076
[45] Date of Patent: Dec. 9, 1997

[54] 5-LIPOXYGENASE-ACTIVATING PROTEIN II

[75] Inventors: Reiner L. Gentz, Gaithersburg, Md.; Robert D. Fleischmann, Washington, D.C.

[73] Assignee: Human Genome Sciences, Inc., Rockville, Md.

[21] Appl. No.: 264,003

[22] Filed: Jun. 22, 1994

[51] Int. Cl.$^6$ .......................... A61K 38/16; C12N 15/12
[52] U.S. Cl. .......................... 514/2; 536/23.5; 530/350; 435/240.1; 435/240.2; 435/240.4; 435/252.3; 514/2
[58] Field of Search .................. 536/23.5; 530/350; 435/320.1, 240.1, 240.2, 240.4, 252.3; 514/2

[56] References Cited

U.S. PATENT DOCUMENTS 5,182,367  1/1993  Gillard et al. ............... 530/350
5,229,516  7/1993  Musser et al. ............... 546/172

OTHER PUBLICATIONS

Jakobsson, P.J., et al., On the Expression and Regulation of 5-lipoxygenase in human lymphocytes, PNAS USA, 89:2521-5 (1992).

Vickers, P.J., et al., Identification of amino acid residues of 5-lipoxygenase-activating protein essential for the binding of leukotriene biosynthesis inhibitors, Mol. Pharmocol., 42:94-102 (1992).

Vickers, P.J. et al., Cross-species Comparison of 5-lipoxygenase- activating protein, Mol. Pharmocol, 42:1014-9 (1992).

Bennet, C.F., et al., Regulation of 5-lipoxygenase and 5-lipoxygenase-activating protein expression in HL60 cells, Biochem. J., 289 (pt. 1):33-9 (1993).

Rifai, A., et al., Expression of 5-lipoxygenase and 5-lipoxygenase activation protein in glomerulonephritis, Kidney Int. Suppl., 39:S95-9 (1993).

Vickers, P.J. et al., Amino Acid Residues of 5-lipoxygenase-activating protein critical for the binding of leukotriene biosynthesis inhibitors, J. Lipid Mediat., 6:31-42 (1993).

Primary Examiner—Keith D. Hendricks
Attorney, Agent, or Firm—Elliot M. Olstein

[57] ABSTRACT

Disclosed is a human FLAP II polypeptide and DNA (RNA) encoding such polypeptide. Also provided is a procedure for producing such polypeptide by recombinant techniques. Further, antagonist/inhibitors against such polypeptide are disclosed. Such antagonist/inhibitors may be used for therapeutic purposes, for example, for treating inflammation, bronchial asthma and may also be used as gastric cytoprotective agents and to treat human glomerulonephritis.

27 Claims, 3 Drawing Sheets

FIG. 1

```
ATGGCGGGAACTCGATCCTGCTGCTGTCTATTCTCTCGGCCTGTCAGCAAAGT
 M  A  G  N  S  I  L  L  A  A  V  S  I  L  S  A  C  Q  Q  S

TATTTTGCTTTGCAAGTTGGAAAGGCAAGATTAAAATACAAGTTACGCCCCAGCAGTC
 Y  F  A  L  Q  V  G  K  A  R  L  K  Y  K  V  T  P  P  A  V

ACTGGGTCACCAGAGTTTGAGAGAGTATTTCGGCACAACAAAACTGTGGAGTTTTAT
 T  G  S  P  E  F  E  R  V  F  R  A  Q  Q  N  C  V  E  F  Y

CCTATATTCATAATTACATTGTGTGGATGGCTGGGTGTATTCAACCAAGTTTTTGCTACT
 P  I  F  I  I  T  L  W  M  A  G  W  Y  F  N  Q  V  F  A  T

TGTCTCGGGTCTGGTACATATATGGCCGTCACCTATACTTCTGGGGATATTCAGAAGCT
 C  L  G  L  V  Y  I  Y  G  R  H  L  Y  F  W  G  Y  S  E  A

GCTAAAAAACGGATCACCGGTTTCCGACTGAGTCTGGGGATTTTGGCCTTGTTGACCCTC
 A  K  K  R  I  T  G  F  R  L  S  L  G  I  L  A  L  L  T  L

CTAGGTGCCCTGGGAATTGCAAACAGCTTTCTGGATGAATATCTGGACCTCAATATTGCC
 L  G  A  L  G  I  A  N  S  F  L  D  E  Y  L  D  L  N  I  A

AAGAAACTGAGGCGGCAATTCTAA
 K  K  L  R  R  Q  F  *
```

FIG. 2

```
  1 ....MAGNSILLAAVSILSACQQSYFALQVGKARLKYKVTPPAVTGSPEF  46
           ::  |:::|::  |::|:|:|  ::|  |  ::|
  1 MDQETVGNVVLLAIVTLISVVQNGFFAHKVEHESRTQNGRSFQRTGTLAF  50

47 ERVFRAQQNCVEFYPIFITTLWMAGWYFNQVFATCLGLVYIYGRHLYFWG  96
    |||  |:||||  |  |::|||:|:|:|||||:||||||||||:|:||
 51 ERVYTANQNCVDAYPTFLAVLWSAGLLCSQVPAAFAGLMYLFVRQKYFVG  100

97 YSEAAKKRITGFRLSLGILALLTLLGALGIANSFLD......EYLDLNIA  140
    |  :: |:|  |::|  |:  ::||:|||  ::|:|      :|||||:
101 YLGERTQSTPGYIFGKRIILFLMSVAGIFNYYLIFFGSDFENYIKTIS   150

141 KKLRRQF... 147
    :::: |:|
151 TTISPLLIP  160
```

Quality:    94.8            Length:        160
Ratio:       0.645           Gaps:            1
Percent Similarity: 51.020   Percent Identity: 34.014

5-LIPOXYGENASE-ACTIVATING PROTEIN II

This invention relates to newly identified polynucleotides, polypeptides encoded by such polynucleotides, the use of such polynucleotides and polypeptides, as well as the production of such polynucleotides and polypeptides. More particularly, the polypeptide of the present invention is 5-lipoxygenase-activating protein II (FLAP II). The invention also relates to inhibiting the action of such polypeptides.

Leukotrienes (LTs), formed in granulocytes, monocytes/macrophages and mast cells, mediate immunological and inflammatory responses. Increased levels of LTs in clinical samples implicate these compounds in a number of hypersensitivity and inflammatory diseases, including asthma and inflammatory bowel disease (Ford-Hutchinson, et al., in: Leukotrienes and Lipoxygenases, J. Rokach, ed., Elsevier Science Publishing, New York, 405–425 (1989); Konig, et al., Eicosanoids 3: 1–22; Robinson and Holgate Adv. Prostaglandin Thromboxane Leukotriene Res. 20:209–216, (1990).

Recently, much attention has been given to the LTs as the major pathophysiologic mediators of the inflammatory response since they are much more potent than the prostaglandins (PGs) with regard to increasing vascular permeability, adhesion of leukocytes to the vessel wall, and edema production. Inhibitors of LT synthesis are currently being developed for possible clinical applications as anti-inflammatory agents. Recent studies appear to place the LTs rather than PGs as the most central agents in the etiologic genesis of bronchial asthma. They have been identified as the agents formerly known as slow-reacting substance and have 200 to 20,000 times the bronchoconstrictor activity as histamine. It is currently believed that an LT antagonist or synthesis inhibitor holds great promise in the treatment of bronchial asthma. LTs have been shown to increase insulin secretion and an alternate current hypothesis is that carbohydrate intolerance in some patients with diabetes mellitus may result from an imbalance in the PG to LT ratio in the islet cell.

The first two steps in the biosynthesis of LTs are catalyzed by the $Ca^{2+}$ and ATP-dependent enzyme 5-lipoxygenase (5-LO) which catalyzes the conversion of arachidonic acid to 5-hydroperoxy-6,8,11,14-eicosatetraeonic acid (5HPETE), and subsequently to leukotriene $A_4$ (Samuelson, et al., Science 237:1171–1176, (1987)). Prostaglandins are also synthesized from arachidonic acid precursors. Aspirin-like drugs, and other enzymes, are efficient at preventing prostaglandin synthesis from arachidonic acid to prevent inflammation and generally relieve pain. However, these aspirin-like drugs and other enzymes are ineffective for preventing the synthesis of LTs from arachidonic acid. The $Ca^{2+}$-dependent translocation of 5-LO from the cytosolic to a membrane fraction appears to be a critical step in the activation of the enzyme (Rouzer and Kargman, J. Biol. Chem. 263:10980–10988, Wong, et al., Biochemistry 27:6763–6769, (1988)). Indole and quinoline classes of LT biosynthesis inhibitors and a series of structural hybrids of these compounds block this membrane association but have no significant inhibitory effect on 5-LO in cell free assays. MK-886 (Gillard, et al., Can. J. Physiol. Pharmacol. 67:456–464, (1989)) and MK-0591 (Brideau, et al., Ca. J. Physiol. Pharmacol. 70:799–807, (1992)) are potent members of these inhibitors. FLAP has been identified as the cellular target of this class of inhibitors (Miller, et al., Nature, 343:278–281, (1990)). Inhibitors which bind to FLAP may directly compete with 5-LO for binding to the protein or may cause a conformational change in FLAP leading to a decreased affinity of 5-LO for its membrane binding site.

cDNA clones for FLAP have been isolated from several species (human, mouse, horse, pig, sheep, rabbit, rat and mouse, see: Vickers, et al., Mol. Pharmacology 42:1014–1019 (1992)). The deduced amino acid sequences correspond to hydrophobic proteins with three potential membrane-spanning domains.

The polypeptide of the present invention is functionally related to FLAP and stimulates 5-LO activity.

In accordance with one aspect of the present invention, there is provided a novel mature polypeptide which is FLAP II, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptide by recombinant techniques.

In accordance with yet a further aspect of the present invention, there is provided a process for utilizing such polypeptide, or polynucleotide encoding such polypeptide to identify substances preventing the interaction of FLAP II with 5-lipoxygenase and to develop inhibitors for the biosynthesis of LTs.

In accordance with yet a further aspect of the present invention, there is provided an antibody against such polypeptides.

In accordance with yet another aspect of the present invention, there are provided antagonist/inhibitors to such polypeptides, which may be used to inhibit the action of such polypeptides, for example, in the treatment of angina, endotoxic shock, inflammatory conditions, such as psoriasis, atopic eczema, rheumatoid arthritis, inflammatory bowel disease, osteoarthritis, tendinitis, bursitis, ulcerative colitis and other immediate hypersensitive reactions, and LT-mediated naso-bronchial obstructive air-passageway conditions, such as allergic bronchoasthma, allergic rhinitis, allergic conjunctivitis, for the treatment of human glomerulonephritis, migraine headaches and as a gastric cytoprotective agent.

These and other aspects of the present invention should be apparent to those skilled in the art from the teachings herein.

The following drawings are illustrative of embodiments of the invention and are not meant to limit the scope of the invention as encompassed by the claims.

FIG. 1 depicts the polynucleotide sequence and corresponding deduced amino acid sequence of FLAP II. The FLAP II polypeptide as shown is the mature polypeptide consisting of 147 amino acids. The standard one-letter abbreviation for amino acids is used.

FIG. 2 shows an amino acid comparison between FLAP II (upper line) and human FLAP I (lower line).

Figure 3:
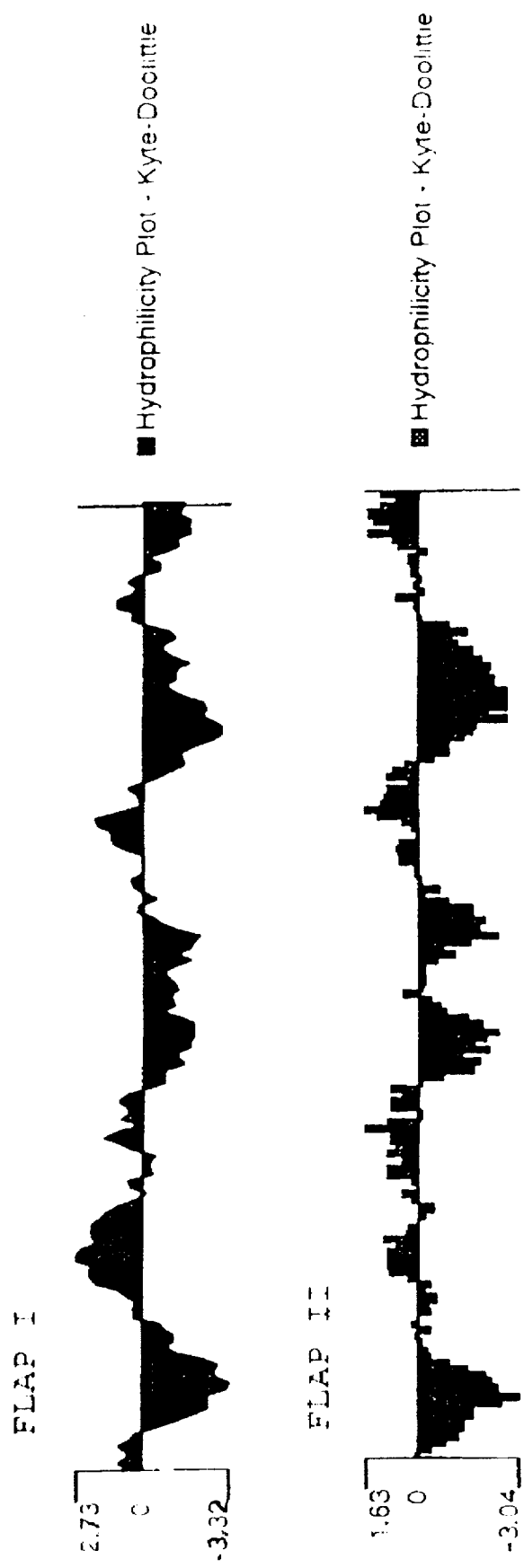
FIG. 3 illustrates the similarity between the hydrophobic and hydrophilic portions of human FLAP I and FLAP II.

In accordance with an aspect of the present invention, there is provided an isolated nucleic acid (polynucleotide) which encodes for the mature polypeptide having the deduced amino acid sequence of FIG. 1 or for the mature polypeptide encoded by the cDNA of the clone deposited as ATCC Deposit No. 75771 on May 12, 1994.

The polynucleotide of this invention was discovered in a cDNA library derived from aorta endothelial cells induced with tumor necrosis factor α. It is structurally related to the FLAP family. It contains an open reading frame encoding a protein of 147 amino acid residues. The protein exhibits the highest degree of homology to the human FLAP protein with 34% identity and 51% similarity over the entire coding sequence. Further, there is a highly conserved region of FLAP I across many different species (residues 42–61) (Vickers, P. J., et al., J. Lipid Mediat., 6:31–42 (1993)). The sequences of the present invention show significant homology to this conserved region (55%).

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or that of the deposited clone or may be a different coding sequence which coding sequence, as a result of the redundancy or degeneracy of the genetic code, encodes the same, mature polypeptide as the DNA of FIG. 1 or the deposited cDNA.

The polynucleotide which encodes for the mature polypeptide of FIG. 1 or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode for a fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a FLAP II polypeptide which has the deduced amino acid sequence of FIG. 1 or which has the amino acid sequence encoded by the deposited cDNA, as well as fragments, analogs and derivatives of such polypeptide.

The terms "fragment," "derivative" and "analog" when referring to the polypeptide of FIG. 1 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the FLAP II genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include $E.$ $coli,$ $Bacillus$ $subtilis,$ $Salmonella$ $typhimurium$ and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The FLAP II polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

FLAP II shows homology to human FLAP I as shown in FIGS. 2 and 3. In FIG. 3, a comparison of hydrophylicity of human FLAP II with human FLAP I shows similar hydrophobic and hydrophilic regions which suggests that FLAP II is functionally related to FLAP I.

The polypeptide of the present invention is also useful for identifying other molecules which have similar biological activity. An example of a screen for this is isolating the coding region of the FLAP II gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention also provides a method of screening drugs to identify those which block (antagonists) interaction of FLAP II to 5-LO. As an example, membrane preparations containing the FLAP II protein would be incubated with a potential drug. The ability of the drug to block the conversion of arachidonic acid could then be measured.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The present invention is also directed to antagonist/inhibitors of the polypeptides of the present invention, which reduce or eliminate the function of the polypeptide.

An example is an antibody against the polypeptide, or in some cases an oligonucleotide, which binds to the polypeptide. Peptide derivatives of FLAP II which have no biological function will recognize and bind to the substrate and thereby prevent the action of FLAP II.

Inhibitors include antisense constructs prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of FLAP II. The antisense RNA oligonucleotide hybridizes to the mRNA in vivo and blocks translation of the mRNA molecule into the FLAP II (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of FLAP II.

Another example of an inhibitor is a small molecule which binds to the active receptor site of FLAP II thereby making it inaccessible to 5-LO such that 5-LO is not activated and does not catalyze the production of LTs. Examples of small molecules include but are not limited to small peptides or peptide-like molecules.

The antagonist/inhibitors may, therefore, be used to treat angina, endotoxic shock, inflammatory conditions, such as psoriasis, atopic eczema, rheumatoid arthritis, ulcerative colitis and other immediate hypersensitive reactions. These antagonist/inhibitors may also be used to treat LT-mediated nasobronchial obstructive air-passageway conditions, such as allergic bronchial asthma, allergic rhinitis and allergic conjunctivitis. They may also be used as gastric cytoprotective agents. The antagonist/inhibitors of the present invention may also be used to treat migraine headaches and human glomerulonephritis, since LTs cause diffuse inflammatory changes in the glomeruli which leads to proteinuria, hypertension and edema. Diabetes mellitus may also be treated with the antagonist/inhibitors since carbohydrate intolerance in patients with diabetes mellitus may result from an excessive imbalance of LT to PG in the islet cell. The antagonist/inhibitors may be employed in a composition with a pharmaceutically acceptable carrier, e.g., as hereinabove described.

When the antagonist/inhibitor compounds of the invention are employed in the treatment of allergic airway disorders, as anti-inflammatory agents and/or as cytoprotective agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter, the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The present invention is also directed to an assay which measures the ability of compounds to inhibit the interaction of FLAP II with 5-LO. Human osteosarcoma cell lines are transfected with DNA for FLAP II and 5-LO. The cells are then treated with the $Ca^{2+}$ ionophore A23187 resulting in significant production of 5-LO products. Cells are then transfected in the presence of potential antagonist/inhibitor compounds and a comparison is done to determine if the level of 5-LO products is reduced. If so, then the compound is an effective antagonist/inhitor of FLAP II by preventing the interaction of FLAP II with 5-LO.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Cloning and expression of FLAP II using *E.coli*

The DNA sequence encoding the FLAP II protein, ATCC #75771, was amplified using PCR oligonucleotide primers corresponding to the 5' and 3' sequences of the gene: The forward primer has the sequence:

CGCGGGATCCGCCGGGAACTCGATCCT-GCTGCTGGCTGCT [SEQ ID NO: 4].

It contains a recognition site for the restriction endonuclease BamHI followed by 27 nucleotides of the FLAP II gene encoding amino acids 2–10. The AUG codon encoding the first methionine is omitted. An initiation codon is provided by the vector pQE-9 (Qiagen, Inc., 9259 Eton Avenue, Chatsworth, Calif. 91311).

The reverse primer has the sequence: GCGCAAGCTTAG AATTTGCCGCCTCAGTTTCTTGGC. [SEQ ID NO: 5].

It contains the last 24 nucleotides complementary to the 3' end of the FLAP II gene followed by a translational stop codon (underlined) and a recognition site for the restriction endonuclease HindIII (in bold).

The amplified sequences were isolated from a 1% agarose gel using a commercially available kit ("Geneclean" BIO 101 Inc., La Jolla, Calif.). The fragment was then digested with the endonucleases BamHI and Asp 718 and then purified again by isolation on a 1% agarose gel. This fragment is designated F1.

pQE-9 encodes antibiotic resistance (Amp'), a bacterial origin of replication (ori), an IPTG-regulatable promoter operator (P/O), a ribosome binding site (RBS), a 6-His-tag and unique restriction enzyme cleavage sites.

4 μg of the plasmid pD10 (Qiagen) were digested with the enzymes BamHI and HindIII and then dephosphorylated using calf intestinal phosphatase using protocols known in the art.

The plasmid was then isolated from a 1% agarose gel using the commercially available kit ("Geneclean"). The dephosphorylated vector DNA is designated V1.

The dephosphorylated vector V1 was ligated with the fragment F1 using T4 DNA ligase using procedures known in the art. The ligation mixture was then transformed into E.coli M15 (described as strain OZ 291 by Villarejo et al. in J. Bacteriol. 210:466–474 [1974]containing the repressor plasmid pDML1 (Certa et al. 1986, EMBO Journal 5:30513056). M15/pDML1 contains multiple copies of the plasmid pDML1, which expresses the lacI repressor and also confers kanamycin resistance (Kan').

Plasmids of transformed bacteria were then isolated and characterized for the correct insertion of the FLAP II gene using the restriction enzymes BamHI and HindIII. A plasmid was isolated containing the correct insert and called pHIS-FLAPII.

E.coli M15 cells containing pDML1 were transformed with pHIS-FLAP II and subsequently grown at 37° C. in LB medium (10 g bacto tryptone, 5 g yeast extract, 5 g NaCl per liter) containing 100 mg/l ampicillin and 25 mg/l kanamycin. At an optical density at 600 nm of 0.8 IPTG was added to a final concentration of 2 mM. After additional 2.5 hours at 37° C. the cells were harvested by centrifugation.

The FLAP II protein expressed in E.coli was purified by Ni-chelate affinity chromatography. The E.coli cells of 1 liter induced culture were lysed by adding buffer A (6M guanidine-hydrochloride, 0.1M sodium phosphate, pH 8.0) and stirring the suspension for 2 hours (100 rpm). The suspension was then centrifuged for 10 minutes at 100000× g. The supernatant was loaded onto a column containing 3 ml of the NTA-resin (Qiagen Inc.). Then, the column was washed with 30 ml of buffer A. Subsequently, the column was washed with 20 ml of buffer B (8M urea, 0.1M sodium phosphate, 0.01M Tris, pH 8.0), and then with 20 ml of buffer B, pH 6.5. Finally, the FLAP II protein was eluted with buffer B, pH 4.5. The presence of the FLAP II protein was confirmed by SDS-PAGE, (Laemmli, Nature 227, 680–685 (1970). Descriptions for the purification of various His-tagged proteins can be found in Hochuli et al., J. Chromatography 411:177–184 (1984), Hochuli et al. Bio/Technology 11:1321–1325 and Gentz et al. (1989) Proc. Natl. Acad. Sci. USA 86:821–824.

EXAMPLE 2

Cloning and expression of FLAP II using the baculovirus expression system

The DNA sequence encoding the full length FLAP II protein, ATCC #75771, was amplified using PCR oligonucleotide primers corresponding to the 5' and 3' sequences of the gene:

The 5' primer has the sequence CCGGATCCGCCACC ATGGCCGGGAACTCGATCCT [SEQ ID NO: 6], and contains a BamHI restriction enzyme site (in bold) followed by 6 nucleotides resembling an efficient signal for the initiation of translation in eukaryotic cells (J. Mol. Biol. 1987, 196, 947–950, Kozak, M.), and just behind the first 20 nucleotides of the FLAP II gene (the initiation codon for translation "ATG" is underlined).

The 3' primer has the sequence CACAGGTACCAGCT TCTGCAAGCATTAAAG [SEQ ID NO: 7], and contains the cleavage site for the restriction endonuclease Asp718 and 20 nucleotides complementary to the 3' non-translated sequence of the FLAP II gene. The amplified sequences were isolated from a 1% agarose gel using a commercially available kit ("Geneclean," BIO 101 Inc., La Jolla, Calif.). The fragment was then digested with the endonucleases BamHI and Asp 718 and then purified as described in Example 1. This fragment is designated F2.

The vector pRG1 (modification of pVL941 vector, discussed below) is used for the expression of the FLAP II protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and Asp718. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pac373, pVL941 and pAcIM1 (Luckow, V. A. and Summers, M. D., Virology, 170:31–39).

The plasmid was digested with the restriction enzymes BamHI and Asp718 and then dephosphorylated using calf intestinal phosphatase by procedures known in the art. The DNA was then isolated from a 1% agarose gel as described in Example 1. This vector DNA is designated V2.

Fragment F2 and the dephosphorylated plasmid V2 were ligated with T4 DNA ligase. E.coli HB101 cells were then transformed and bacteria identified that contained the plasmid (pBacFLAPII) with the FLAP II gene using the enzymes BamHI and Asp718. The sequence of the cloned fragment was confirmed by DNA sequencing.

5 μg of the plasmid pBacFLAPII were cotransfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBacFLAP II were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-FLAP II at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

EXAMPLE 3

Expression of FLAP II in mammalian cells

Fragment F2 described in example 2 was used for the insertion into the mammalian expression vector pCMV11.

Plasmid pCMV11 contains the strong promoter and enhancer of the "major immediate-early" gene of human cytomegalovirus ("HCMV"; Boshart et al., Cell, 41:521–530 (1985)) behind the promoter are single cleavage sites for the restriction endonucleases HindIII, BamHI, PvuII and Asp718. After the Asp718 cleavage site there is situated the polyadenylation site of the preproinsulin gene of the rat (Lomedico et al., Cell, 18:545–558 (1979)). The plasmid contains in addition the replication origin of the SV40 virus and a fragment from pBR322 which confers *E.coli* bacteria ampicillin resistance and the replication in *E.coli*. Plasmid pCMV11 was digested with BamHI and asp718 and then dephosphorylated using calf intestinal phosphatase as described in Example 1. The dephosphorylated vector was thereafter isolated from an agarose gel as described in Example 1.

The vector fragment V3 was ligated with fragment F2, *E.coli* HB101 bacteria were transformed and the plasmids of the transformed cells isolated by procedures known in the art. By means of restriction analysis and DNA sequencing according to known methods, transformants were identified which contained the plasmid with the insert in the correct orientation. This vector received the designation pCMV-FLAP II.

Transfections of the COS1 (ATCC CRL 1650) Raji-(ATCC CRL 8163) and Jurkart-(ATCC CCL 86) cells with the plasmid pCMV-FLAP II were carried out either according to the lipofection method published by Felgner et al. (Proc. Natl. Acad. Sci. USA 84:7413–7417 (1987)) or by the well known technique using DEAE Dextran (Pharmacia). The expression vector pCMV11 without the FLAP II gene served as a control. 72 hours after the transfections were carried out the cells were harvested and analyzed for the activation of 5-lipoxygenase.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least 95% identity to a member selected from the group consisting
   (a) a polynucleotide encoding a polypeptide comprising amino acid 2 to 147 of SEQ ID NO:2; and
   (b) the complement of (a).

2. The isolated polynucleotide of claim 1 wherein said member is (a).

3. The isolated polynucleotide of claim 1 wherein said member is (a) and the polypeptide comprise amino acids 1 to 147 of SEQ ID NO:2.

4. The isolated polynucleotide of claim 1 comprising a polynucleotide encoding a polypeptide comprising the amino acid sequence identical to amino acids 2 to 147 of SEQ ID NO:2.

5. The isolated polynucleotide of claim 1, wherein the polynucleotide is DNA.

6. The isolated polynucleotide of claim 1 comprising a polynucleotide encoding a polypeptide comprising the amino sequence identical to amino acids 1 to 147 of SEQ ID NO:2.

7. The isolated polynucleotide of claim 1, wherein said polynucleotide is RNA.

8. A method of making a recombinant vector comprising inserting the isolated polynucleotide of claim 2 into a vector, wherein said polynucleotide is DNA.

9. A recombinant vector comprising the polynucleotide of claim 2, wherein said polynucleotide is DNA.

10. A recombinant host cell comprising the polynucleotide of claim 2, wherein said polynucleotide is DNA.

11. A method for producing a polypeptide comprising expressing from the recombinant cell of claim 10 the polypeptide encoded by said polynucleotide.

12. A process for producing a polypeptide comprising:
   expressing from a recombinant cell containing the polynucleotide of claim 4 the polypeptide encoded by said polynucleotide.

13. A process for producing a polypeptide comprising:
   expressing from a recombinant cell containing the polynucleotide of claim 6 the polypeptide encoded by said polynucleotide.

14. The isolated polynucleotide of claim 1 comprising nucleotides 4 to 441 of SEQ ID NO:1.

15. The isolated polynucleotide of claim 1 comprising nucleotides 1 to 444 of SEQ ID NO:1.

16. The isolated polynucleotide of claim 1 comprising the nucleotides of the sequence of SEQ ID NO:1.

17. An isolated polynucleotide comprising a polynucleotide having at least a 95% identity to a member selected from the group consisting of:
   (a) a polynucleotide encoding the same mature polypeptide encoded by the human cDNA in ATCC Deposit No. 75771; and
   (b) the complement of (a).

18. The isolated polynucleotide of claim 17, wherein the member is (a).

19. The isolated polynucleotide of claim 17, wherein said polynucleotide comprises DNA identical to the coding portion of the human cDNA in ATCC Deposit No. 75771 which encodes a mature polypeptide.

20. An isolated polypeptide comprising:
   a mature polypeptide having an amino acid sequence encoded by a polynucleotide which is at least 95% identical to the polynucleotide of claim 4.

21. The isolated polypeptide of claim 20, comprising amino acids 2 to 147 of sequence of SEQ ID NO:2.

22. The isolated polypeptide of claim 20, comprising amino acids 1 to 147 of sequence of SEQ ID NO:2.

23. The isolated polypeptide of claim 20 comprising amino acids 1 to 147 of SEQ ID NO:2.

24. An isolated polypeptide comprising:
   a mature polypeptide encoded by a polynucleotide which is at least 95% identical to the human cDNA contained in ATCC Deposit No. 75771.

25. The isolated polypeptide of claim 24 comprising the mature polypeptide encoded by the human cDNA in ATCC Deposit No. 75771.

26. A method for the treatment of a patient having need to inhibit a FLAP II polypeptide comprising:
   administering to the patient a therapeutically effective amount of the compound of claim 20.

27. A method for the treatment of a patient having need to inhibit a FLAP II polypeptide comprising:
   administering to the patient a therapeutically effective amount of the compound of claim 24.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 444 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 1..441

( x i ) SEQUENCE DESCRIPTION: SEQ ID NO:1:

```
ATG  GCC  GGG  AAC  TCG  ATC  CTG  CTG  GCT  GCT  GTC  TCT  ATT  CTC  TCG  GCC         4 8
Met  Ala  Gly  Asn  Ser  Ile  Leu  Leu  Ala  Ala  Val  Ser  Ile  Leu  Ser  Ala
 1                 5                      10                      15

TGT  CAG  CAA  AGT  TAT  TTT  GCT  TTG  CAA  GTT  GGA  AAG  GCA  AGA  TTA  AAA         9 6
Cys  Gln  Gln  Ser  Tyr  Phe  Ala  Leu  Gln  Val  Gly  Lys  Ala  Arg  Leu  Lys
```

|  | 20 |  |  |  |  | 25 |  |  |  |  | 30 |  |  |  |
|---|---|---|---|---|---|---|---|---|---|---|---|---|---|---|
| TAC | AAA | GTT | ACG | CCC | CCA | GCA | GTC | ACT | GGG | TCA | CCA | GAG | TTT | GAG | AGA | 144
| Tyr | Lys | Val | Thr | Pro | Pro | Ala | Val | Thr | Gly | Ser | Pro | Glu | Phe | Glu | Arg |
|  |  | 35 |  |  |  |  | 40 |  |  |  |  | 45 |  |  |  |

```
TAC AAA GTT ACG CCC CCA GCA GTC ACT GGG TCA CCA GAG TTT GAG AGA        144
Tyr Lys Val Thr Pro Pro Ala Val Thr Gly Ser Pro Glu Phe Glu Arg
         35              40               45

GTA TTT CGG GCA CAA CAA AAC TGT GTG GAG TTT TAT CCT ATA TTC ATA        192
Val Phe Arg Ala Gln Gln Asn Cys Val Glu Phe Tyr Pro Ile Phe Ile
         50              55               60

ATT ACA TTG TGG ATG GCT GGG TGG TAT TTC AAC CAA GTT TTT GCT ACT        240
Ile Thr Leu Trp Met Ala Gly Trp Tyr Phe Asn Gln Val Phe Ala Thr
 65              70               75                            80

TGT CTG GGT CTG GTG TAC ATA TAT GGC CGT CAC CTA TAC TTC TGG GGA        288
Cys Leu Gly Leu Val Tyr Ile Tyr Gly Arg His Leu Tyr Phe Trp Gly
                 85              90                        95

TAT TCA GAA GCT GCT AAA AAA CGG ATC ACC GGT TTC CGA CTG AGT CTG        336
Tyr Ser Glu Ala Ala Lys Lys Arg Ile Thr Gly Phe Arg Leu Ser Leu
             100             105                  110

GGG ATT TTG GCC TTG TTG ACC CTC CTA GGT GCC CTG GGA ATT GCA AAC        384
Gly Ile Leu Ala Leu Leu Thr Leu Leu Gly Ala Leu Gly Ile Ala Asn
         115             120                  125

AGC TTT CTG GAT GAA TAT CTG GAC CTC AAT ATT GCC AAG AAA CTG AGG        432
Ser Phe Leu Asp Glu Tyr Leu Asp Leu Asn Ile Ala Lys Lys Leu Arg
         130             135                  140

CGG CAA TTC TAA                                                        444
Arg Gln Phe
145
```

( 2 ) INFORMATION FOR SEQ ID NO:2:

( i ) SEQUENCE CHARACTERISTICS:
        ( A ) LENGTH: 147 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Gly Asn Ser Ile Leu Leu Ala Ala Val Ser Ile Leu Ser Ala
 1               5                  10                  15

Cys Gln Gln Ser Tyr Phe Ala Leu Gln Val Gly Lys Ala Arg Leu Lys
             20                  25                  30

Tyr Lys Val Thr Pro Pro Ala Val Thr Gly Ser Pro Glu Phe Glu Arg
         35              40                  45

Val Phe Arg Ala Gln Gln Asn Cys Val Glu Phe Tyr Pro Ile Phe Ile
         50              55                  60

Ile Thr Leu Trp Met Ala Gly Trp Tyr Phe Asn Gln Val Phe Ala Thr
 65              70                  75                       80

Cys Leu Gly Leu Val Tyr Ile Tyr Gly Arg His Leu Tyr Phe Trp Gly
                 85                  90                  95

Tyr Ser Glu Ala Ala Lys Lys Arg Ile Thr Gly Phe Arg Leu Ser Leu
             100                 105                 110

Gly Ile Leu Ala Leu Leu Thr Leu Leu Gly Ala Leu Gly Ile Ala Asn
             115                 120                 125

Ser Phe Leu Asp Glu Tyr Leu Asp Leu Asn Ile Ala Lys Lys Leu Arg
         130                 135                 140

Arg Gln Phe
145
```

( 2 ) INFORMATION FOR SEQ ID NO:3:

( i ) SEQUENCE CHARACTERISTICS:

(A) LENGTH: 160 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:3:

| Met | Asp | Gln | Glu | Thr | Val | Gly | Asn | Val | Val | Leu | Leu | Ala | Ile | Val | Thr |
|---|---|---|---|---|---|---|---|---|---|---|---|---|---|---|---|
| 1 | | | | 5 | | | | | 10 | | | | | 15 | |
| Leu | Ile | Ser | Val | Val | Gln | Asn | Gly | Phe | Phe | Ala | His | Lys | Val | Glu | His |
| | | | 20 | | | | | 25 | | | | | 30 | | |
| Glu | Ser | Arg | Thr | Gln | Asn | Gly | Arg | Ser | Phe | Gln | Arg | Thr | Gly | Thr | Leu |
| | | 35 | | | | | 40 | | | | 45 | | | | |
| Ala | Phe | Glu | Arg | Val | Tyr | Thr | Ala | Asn | Gln | Asn | Cys | Val | Asp | Ala | Tyr |
| | 50 | | | | | 55 | | | | | 60 | | | | |
| Pro | Thr | Phe | Leu | Ala | Val | Leu | Trp | Ser | Ala | Gly | Leu | Leu | Cys | Ser | Gln |
| 65 | | | | | 70 | | | | | 75 | | | | | 80 |
| Val | Pro | Ala | Ala | Phe | Ala | Gly | Leu | Met | Tyr | Leu | Phe | Val | Arg | Gln | Lys |
| | | | | 85 | | | | | 90 | | | | | 95 | |
| Tyr | Phe | Val | Gly | Tyr | Leu | Gly | Glu | Arg | Thr | Gln | Ser | Thr | Pro | Gly | Tyr |
| | | | 100 | | | | | 105 | | | | | 110 | | |
| Ile | Phe | Gly | Lys | Arg | Ile | Ile | Leu | Phe | Leu | Phe | Leu | Met | Ser | Val | Ala |
| | | 115 | | | | | 120 | | | | | 125 | | | |
| Gly | Ile | Phe | Asn | Tyr | Tyr | Leu | Ile | Phe | Phe | Gly | Ser | Asp | Phe | Glu | Asn |
| | 130 | | | | | 135 | | | | | 140 | | | | |
| Tyr | Ile | Lys | Thr | Ile | Ser | Thr | Thr | Ile | Ser | Pro | Leu | Leu | Leu | Ile | Pro |
| 145 | | | | | 150 | | | | | 155 | | | | | 160 |

(2) INFORMATION FOR SEQ ID NO:4:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

CGCGGGATCC GCCGGGAACT CGATCCTGCT GCTGGCTGCT                40

(2) INFORMATION FOR SEQ ID NO:5:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

GCGCAAGCTT AGAATTGCCG CCTCAGTTTC TTGGC                    35

(2) INFORMATION FOR SEQ ID NO:6:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:6:

CCGGATCCGC CACCATGGCC GGGAACTCGA TCCT    34

( 2 ) INFORMATION FOR SEQ ID NO:7:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:7:

CACAGGTACC AGCTTCTGCA AGCATTAAAG    30